United States Patent [19]

Telschow et al.

[11] Patent Number: 5,698,736
[45] Date of Patent: Dec. 16, 1997

[54] HIGH TEMPERATURE, CATALYTIC FRIEDEL-CRAFTS SYNTHESIS OF BENZENE PHOSPHORUS DICHLORIDE

[75] Inventors: Jeffrey E. Telschow, Tarrytown; Alan J. Abramson, Hartsdale, both of N.Y.

[73] Assignee: Akzo Nobel nv, Arnhem, Netherlands

[21] Appl. No.: 792,311

[22] Filed: Jan. 31, 1997

[51] Int. Cl.⁶ ................................................ C07F 9/52
[52] U.S. Cl. ................................................ 562/820
[58] Field of Search ........................ 568/16, 17; 562/820

[56] References Cited

U.S. PATENT DOCUMENTS

| | | | |
|---|---|---|---|
| 3,029,282 | 4/1962 | Toy et al. | 260/543 |
| 3,557,204 | 1/1971 | Weinberg | 562/820 |
| 3,734,958 | 5/1973 | Rio | 260/543 P |
| 3,864,394 | 2/1975 | Via et al. | 260/543 P |
| 3,954,859 | 5/1976 | Jurewicz et al. | 260/543 P |
| 4,409,152 | 10/1983 | Humphrey | 260/543 P |
| 4,436,673 | 3/1984 | Skrzec | 260/543 P |
| 4,521,346 | 6/1985 | Kleiner | 562/820 |
| 4,536,351 | 8/1985 | Neumaier | 260/543 P |
| 4,737,317 | 4/1988 | Wilson | 260/543 P |

FOREIGN PATENT DOCUMENTS

| | | | |
|---|---|---|---|
| 24123 | 2/1981 | European Pat. Off. | C07F 9/52 |
| 101653A | 4/1983 | U.S.S.R. | |

OTHER PUBLICATIONS

K.G. Weinberg, "Synthesis of Arylphosphonous Dichlorides, Diarylphosphinous Chlorides, and 1,6-Diphosphatriptycene from Elemental Phosphorus", J. Org. Chem., vol. 40, No. 24, 1975, pp. 3586–3589.

M.P. Brown et al., "An Improved Method of Preparation for Diphenylchlorophosphine", Chemistry and Industry, Jan. 7, 1961., p. 24. Chemical Abstracts, vol. 119, 72842z (1993).

Derwent Patent Abstract 84–171849/28 (1984).

Primary Examiner—Gary Geist
Assistant Examiner—Jean F. Vollano
Attorney, Agent, or Firm—Richard P. Fennelly; Louis A. Morris

[57] ABSTRACT

Benzene phosphorus dichloride can be prepared by the reaction of benzene and phosphorus trichloride in the presence of a catalytically effective amount of a Friedel-Crafts catalyst, such as aluminum trichloride or ferric trichloride, at elevated temperature, such as from about 200° C. to about 250° C., and superatmospheric pressure, such as no less than the vapor pressure of the components at the chosen reaction temperature, to insure a liquid reaction medium.

7 Claims, No Drawings

HIGH TEMPERATURE, CATALYTIC FRIEDEL-CRAFTS SYNTHESIS OF BENZENE PHOSPHORUS DICHLORIDE

BACKGROUND OF THE INVENTION

Benzene phosphorus dichloride (which is also named "phenylphosphonous dichloride") or "BPD" can be made by a variety of techniques including the following:

U.S. Pat. No. 3,029,282 to A.D.F. Toy et al. describes the synthesis of BPD by the reaction of phosphorus trichloride and benzene at elevated temperatures in the presence of monochlorobenzene;

U.S. Pat. No. 3,734,958 to A. Rio describes the use of white phosphorus and a chlorine-containing organic compound to make BPD at temperatures of 200° C. to 400° C. at either atmospheric or superatmospheric pressure;

F. A. Via et al. in U.S. Pat. No. 3,864,394 describe the manufacture of BPD in an autoclave by reacting monochlorobenzene, phosphorus trichloride and elemental phosphorus;

U.S. Pat. No. 4,409,152 to L. F. Humphrey covers the continuous reaction of monochlorobenzene, phosphorus trichloride and elemental phosphorus at elevated pressures and temperatures to form BPD;

BPD is described as being made in an electrically heated fluid bed reactor from phosphorus trichloride and benzene in U.S. Pat. No. 4,436,673 to A. E. Skrzec; and K. G. Weinberg in the Journal of Organic Chemistry, Vol. 40, No. 24, 1975, pp. 3586–3589 describes the manufacture of BPD by heating elemental phosphorus in an excess of chlorobenzene in a sealed glass tube at 350° C. for several hours.

DESCRIPTION OF THE INVENTION

The present invention relates to the preparation of benzene phosphorus dichloride by the reaction of benzene and phosphorus trichloride in the presence of a catalytically effective amount of a Friedel-Crafts catalyst at elevated temperature and at superatmospheric pressure to insure a liquid reaction medium.

The relative amounts of benzene and phosphorus trichloride to use in accordance with the present process will, in general, range from about 1:1 to about 1:6 on a molar basis.

The amount of Friedel-Crafts catalyst to use in the process of the present invention will be a catalytically effective amount and will, in general, range from about 1% to about 25%, by mole of the benzene. Representative Friedel-Craft catalysts that can be employed include those known to persons of ordinary skill in the art with representative catalysts of this type being aluminum trichloride and ferric trichloride.

The reaction conditions which are to be used are elevated temperatures of, in general, from about 150° C. to about 300° C., and superatmospheric pressure (e.g., no less than the vapor pressure of the components at the chosen reaction temperature) to keep the reactants in the liquid state at such temperatures.

The process of this invention is further illustrated by the Examples which follow.

EXAMPLES 1–14

The reactor used in these Examples consisted of an unstirred stainless steel pipe reactor connected to an apparatus for regulating, measuring and releasing nitrogen (plus HCl) pressure in the system. Nitrogen pressures of at least 50 psi greater than the calculated reactant vapor pressures at the desired reaction temperature were employed. Toward the end of the runs, a pressure of 500 psi was routinely used.

Catalyst (100 mg $AlCl_3$, which is 5 mol %), 1.34 mL (15.0 mmol) of benzene, and 2.62 mL (30.0 mmol) of $PCl_3$ were charged in a dry box to a dried reactor tube. A silicone oil bath heated the tube, and a thermocouple measured actual reaction temperature. For analysis of the reaction, the entire reactor contents were transferred in the dry box to a bottle sealed with a crimped-on septum. Gas chromatographic and mass spectral methods were used to analyze the upper liquid layer for the presence of BPD (benzene phosphorus dichloride), PCBs, and benzene. It was presumed that the sediment contained the expected complex of BPD with $AlCl_3$. The results obtained are as follows:

| Catalyst | Amount (mol %) | Temp/Time (°C./hr) | BPD Made (wt %) | Benzene (wt %) | PCBs (ppm) |
|---|---|---|---|---|---|
| $AlCl_3$ | 5 | 200/6 | 2 | — | — |
| " | 5 | 230/6 | 18 | — | — |
| " | 5 | 240/12 | 13.4 | — | ND |
| " | 5 | 250/6 | 6.5 | — | — |
| " | 5 | 240/6 | 11.4 | — | — |
| " | 5 | 250/6 | 25.6 | 14.6 | — |
| " | 5 | 250/6 | 15.2 | 13.7 | — |
| " | 10 | 250/6 | 12.9 | 10.4 | — |
| $FeCl_3$ | 5 | 240/6 | 13 | — | — |
| " | 5 | 250/6 | 4.8 | — | — |
| " | 5 | 250/12 | 1.4 | — | — |
| " | 5 | 260/6 | 3.9 | — | ND |
| " | 10 | 250/6 | 14.6 | 21.3 | ND |

ND = none detected to a limit of about 1 ppm.
The designation "—" in the above table indicates that no analysis for the compound or composition was made.

The wide variability in the results shown in the above Examples is due to the extremely small scale of the reaction that was employed. In such a small scale reaction, small discrepancies in the amounts of reagents used and/or the product recovered will translate into comparatively large variations in the results obtained for weight percentages of product(s) found, for example.

The preceding Examples are presented for illustrative purposes only and, for that reason, should not be construed in a limiting sense. The scope of protection sought is set forth in the Claims which follow.

We claim:

1. A process for the preparation of benzene phosphorus dichloride which comprises the reaction of benzene and phosphorus trichloride in the presence of a catalytically effective amount of a Friedel-Crafts catalyst at elevated temperature and a superatmospheric pressure to insure a liquid reaction medium.

2. A process as claimed in claim 1 wherein the catalyst is aluminum trichloride.

3. A process as claimed in claim 1 wherein the catalyst is aluminum trichloride and the temperature of the reaction is from about 200° C. to about 250° C.

4. A process as claimed in claim 1 wherein the catalyst is aluminum trichloride, the temperature of the reaction is from about 200° C. to about 250° C., and the pressure is no less than the vapor pressure of the components at the chosen reaction temperature.

5. A process as claimed in claim 1 wherein the catalyst is ferric trichloride.

6. A process as claimed in claim 1 wherein the catalyst is ferric trichloride and the temperature of the reaction is from about 200° C. to about 250° C.

7. A process as claimed in claim 1 wherein the catalyst is ferric trichloride, the temperature of the reaction is from about 200° C. to about 250° C., and the pressure is no less than the vapor pressure of the components at the chosen reaction temperature.

* * * * *